US010085902B2

(12) United States Patent
Chia et al.

(10) Patent No.: US 10,085,902 B2
(45) Date of Patent: Oct. 2, 2018

(54) PEDIATRIC TRANSPORT HARNESS FOR AN AMBULANCE COT

(71) Applicant: Ferno Washington, Inc., Wilmington, OH (US)

(72) Inventors: Orlando Chia, Mississauga (CA); Bruce Whitaker, Mississauga (CA)

(73) Assignee: Ferno Washington, Inc., Wilmington, OH (US)

( * ) Notice: Subject to any disclaimer, the term of this patent is extended or adjusted under 35 U.S.C. 154(b) by 260 days.

(21) Appl. No.: 14/266,041

(22) Filed: Apr. 30, 2014

(65) Prior Publication Data

US 2015/0313778 A1 Nov. 5, 2015

(51) Int. Cl.

*A61F 5/37* (2006.01)
*A61G 1/044* (2006.01)
*A61G 1/02* (2006.01)

(52) U.S. Cl.

CPC ................ *A61G 1/044* (2013.01); *A61G 1/02* (2013.01); *A61G 2200/14* (2013.01)

(58) Field of Classification Search

CPC . A47D 13/08; A61G 1/01; A61G 1/04; A61G 1/044; A61G 2200/14; A61G 7/0504; A61G 13/12; A41D 13/0007; B60N 2/2812; A62B 1/02

USPC ........... 5/655, 628, 494, 416, 603, 621, 625; 128/875, 846, 874, 869; 297/464, 467, 297/484, 485

See application file for complete search history.

(56) References Cited

U.S. PATENT DOCUMENTS

| | | | |
|---|---|---|---|
| 2,788,530 | A | 2/1952 | Ferguson |
| 2,589,708 | A | 3/1952 | Koster |
| 4,117,840 | A | 10/1978 | Rasure |
| 4,299,211 | A | 11/1981 | Doynow |
| 4,515,155 | A | 5/1985 | Wagemann |
| 4,657,005 | A | 4/1987 | Williamson |
| 4,665,908 | A | 5/1987 | Calkin |
| 4,979,520 | A | 12/1990 | Boone, Jr. et al. |
| 4,989,286 | A | 2/1991 | Tucker |
| 5,014,724 | A | 5/1991 | Miller |
| 5,233,714 | A | 8/1993 | De Bell Daniel |

(Continued)

FOREIGN PATENT DOCUMENTS

| | | | | |
|---|---|---|---|---|
| DE | 20316498 U1 | 4/2005 | | |
| GB | 2315401 A * | 2/1998 | ........... | A47D 15/008 |

(Continued)

OTHER PUBLICATIONS

PCT International Search Report dated Jul. 31, 2015 for PCT Application No. PCT/US2015/028187 filed Apr. 15, 2015 for Ferno-Washington, Inc., entitled "Pediatric Transport Harness for an Ambulance Cot".

(Continued)

*Primary Examiner* — Ophelia A Hawthorne
*Assistant Examiner* — Caitlin Carreiro
(74) *Attorney, Agent, or Firm* — Dinsmore & Shohl LLP

(57) ABSTRACT

Pediatric transport harness systems for an emergency cot including a harness support structure, a stabilizing strap, guide straps, and a harness restraint. The harness restraint is slidably engaged with the guide straps and is continuously positionable and secureable along the guide straps. Methods of securing a pediatric patient to the emergency cot using the pediatric transport harness system.

17 Claims, 13 Drawing Sheets

(56) References Cited

U.S. PATENT DOCUMENTS

| | | | |
|---|---|---|---|
| 5,439,008 | A | 8/1995 | Bowman |
| 5,496,092 | A | 3/1996 | Williams et al. |
| 6,053,580 | A | 4/2000 | White, Sr. |
| 6,381,785 | B1 | 5/2002 | Mancera Browne et al. |
| 6,708,356 | B1 | 3/2004 | LaValle |
| 6,772,764 | B2 | 8/2004 | Chapman |
| 6,834,405 | B1 | 12/2004 | Hillstead |
| 6,898,811 | B2 | 5/2005 | Zucker et al. |
| 6,966,087 | B2 * | 11/2005 | Robinette ............. A61F 5/3784 5/625 |
| 7,251,846 | B1 | 8/2007 | Elkin et al. |
| 7,770,969 | B2 * | 8/2010 | Boyle .................. B60N 2/2806 297/254 |
| 7,861,341 | B2 | 1/2011 | Ayette et al. |
| 2010/0175702 | A1 | 7/2010 | West |
| 2012/0084920 | A1 | 4/2012 | Zucker et al. |

FOREIGN PATENT DOCUMENTS

| | | | |
|---|---|---|---|
| GB | 2315401 | A | 4/1998 |
| WO | WO9947028 | A1 | 9/1999 |
| WO | WO2009001107 | A1 | 12/2008 |

OTHER PUBLICATIONS iNtegrated Patient Transport & Loading System, fernoems.com/inx; http://www.fernoems.com/~/media/site-us/PDFs/catalog/FERNO_INXbrochPAGE_Ir.ashx.

Model 678 Pedi-Mate User's Manual, Ferno, Pub. No. 234-2045-03, pp. 1-12, Oct. 2011, http://co.grand.co.us/DocumentCenter/View/676.

Neomate Infant Restraint System User's Manual, Ferno, pp. 1-11, http://www.ferno.it/symphony/workspace/uploads/media/images/neomate-manual-final-533bde3e2e2d3.pdf.

* cited by examiner

PEDIATRIC TRANSPORT HARNESS FOR AN AMBULANCE COT

TECHNICAL FIELD

The present disclosure relates generally to pediatric harnesses, and more specifically, to pediatric transport harnesses for emergency cots.

BACKGROUND

Providing effective restraint for pediatric patients in ambulances is a complex problem with many unique and unresolved issues. As the ambulance environment is specifically designed for emergency treatment of passengers, exposure in a crash environment may be more severe to a pediatric patient requiring transport. When transporting a pediatric patient with a medical problem which requires constant monitoring, a current practice is to employ pediatric harnesses for emergency cots for restraining the pediatric patient. However, improvements to such practices are needed, e.g., providing pediatric harness systems which may be adjusted to accommodate varying sizes and weights of pediatric patients and/or which may be adjusted to account for positioning errors in placement of pediatric harness systems onto emergency cots.

SUMMARY

It is against this background that the present disclosure provides pediatric transport harness systems for emergency cots which provide adjustable harness restraints. The adjustable harness restraints may function to accommodate varying sizes and weights of pediatric patients and/or may function to account for positioning errors in placement of the pediatric transport harness systems onto emergency cots.

In one embodiment, a pediatric transport harness system for an emergency cot is disclosed. The pediatric transport harness system includes a harness support structure attachable to the emergency cot, at least one stabilizing strap attached to the harness support structure, at least two guide straps attached to the harness support structure, and a harness restraint attached to the harness support structure. The harness restraint includes a torso harness and a crotch strap attachable to the torso harness. The torso harness includes a pair of torso straps attached to a securing strap. The securing strap is slidably engaged with the guide straps such that the securing strap may be continuously positioned and secured along a length of the at least two guide straps.

In another embodiment, a pediatric transport harness system for an emergency cot is disclosed. The pediatric transport harness system includes a harness support structure attachable to the emergency cot, at least one stabilizing strap attached to the harness support structure, at least two guide straps attached to the upper section of the harness support structure, and a harness restraint attached to the harness support structure. The harness support structure has an upper section, a middle section, and a lower section. The harness restraint is attached to the middle section of the harness support structure. The harness restraint includes a torso harness and a crotch strap attachable to the torso harness. The torso harness includes a pair of torso straps attached to a securing strap and each of the torso straps is attached to the middle section of the harness support structure. The crotch strap is attached to the lower section of the harness support structure. The harness support structure is attachable to the emergency cot via the at least one stabilizing strap and the securing strap. The securing strap is slidably engaged with the at least two guide straps such that the securing strap may be continuously positioned and secured along a length of the at least two guide straps.

In yet another embodiment, a method of securing a patient to an emergency cot using a pediatric transport harness system is disclosed. The method includes attaching the harness support structure to the emergency cot via the at least one stabilizing strap and the securing strap, placing the pediatric patient on the harness support structure, placing the torso harness over the patient, and attaching the torso harness to the crotch strap thereby securing the pediatric patient to the emergency cot. The pediatric transport harness system includes a harness support structure attachable to the emergency cot, at least one stabilizing strap attached to the harness support structure, at least two guide straps attached to the harness support structure, and a harness restraint attached to the harness support structure. The harness restraint includes a torso harness and a crotch strap attachable to the torso harness. The torso harness includes a pair of torso straps attached to a securing strap. The securing strap is slidably engaged with the guide straps such that the securing strap may be continuously positioned and secured along a length of the at least two guide straps.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION

Reference will now be made in detail to embodiments of a pediatric transport harness system. In one or more embodiments, the pediatric transport harness system includes a harness support structure, at least two guide straps, and a harness restraint. In other embodiments, the pediatric transport harness system includes a harness support structure, a stabilizing strap, at least two guide straps, and a harness restraint. The harness restraint may include a torso harness and a crotch strap.

Embodiments of the pediatric transport harness system will be described now with reference to FIGS. 1-14. Thereafter, embodiments of use of the pediatric transport harness system will be described with reference to FIGS. 1-14.

I. Pediatric Transport Harness Systems

Figure 1:
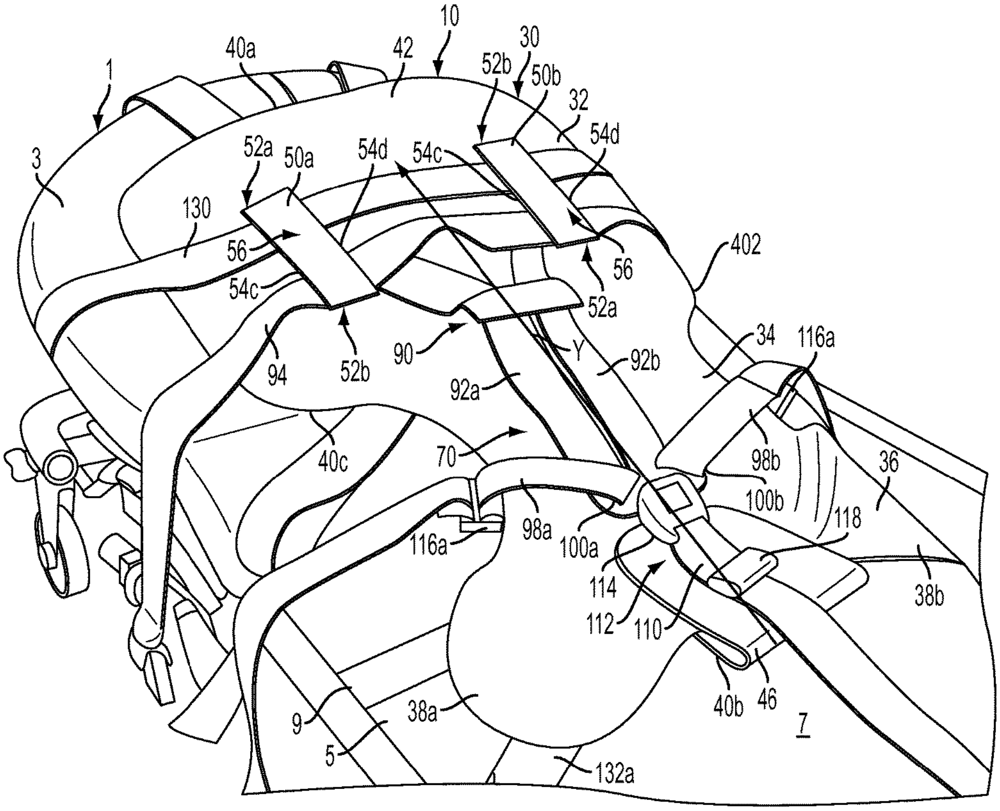
FIG. 1 is a side perspective view of an embodiment of a pediatric transport harness system attached to an emergency cot according to an embodiment of the present disclosure.
Figure 2:
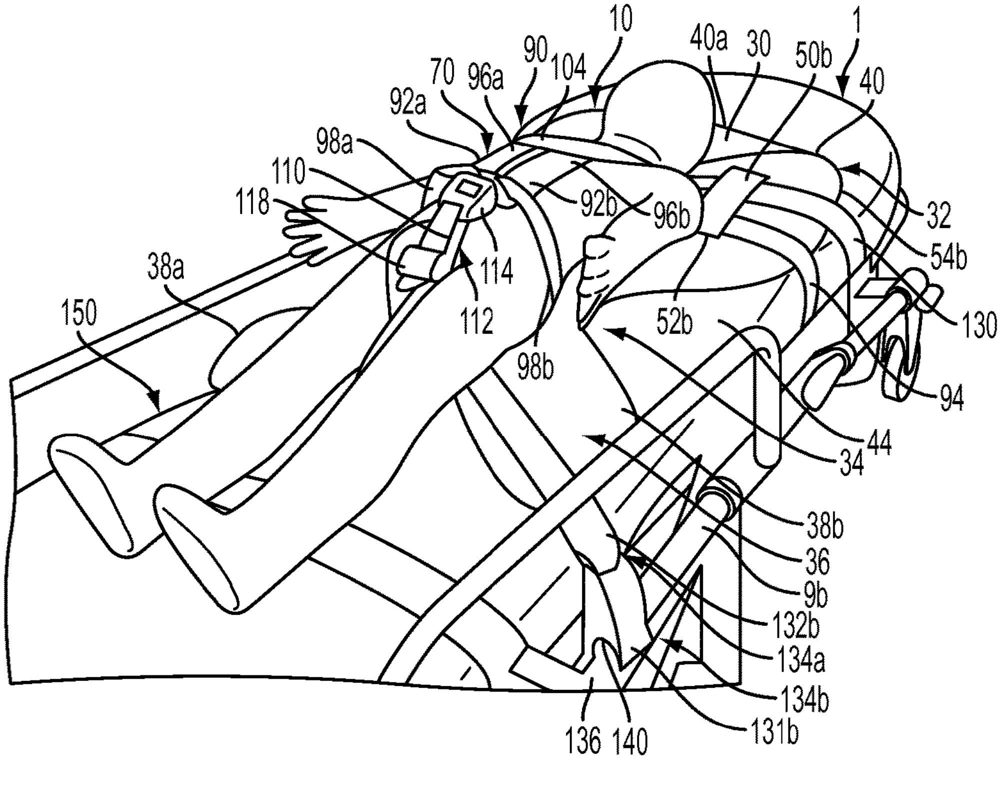
FIG. 2 is a side perspective view of an embodiment of a pediatric transport harness system attached to an emergency cot with a pediatric patient secured thereon according to an embodiment of the present disclosure.
Figure 8:
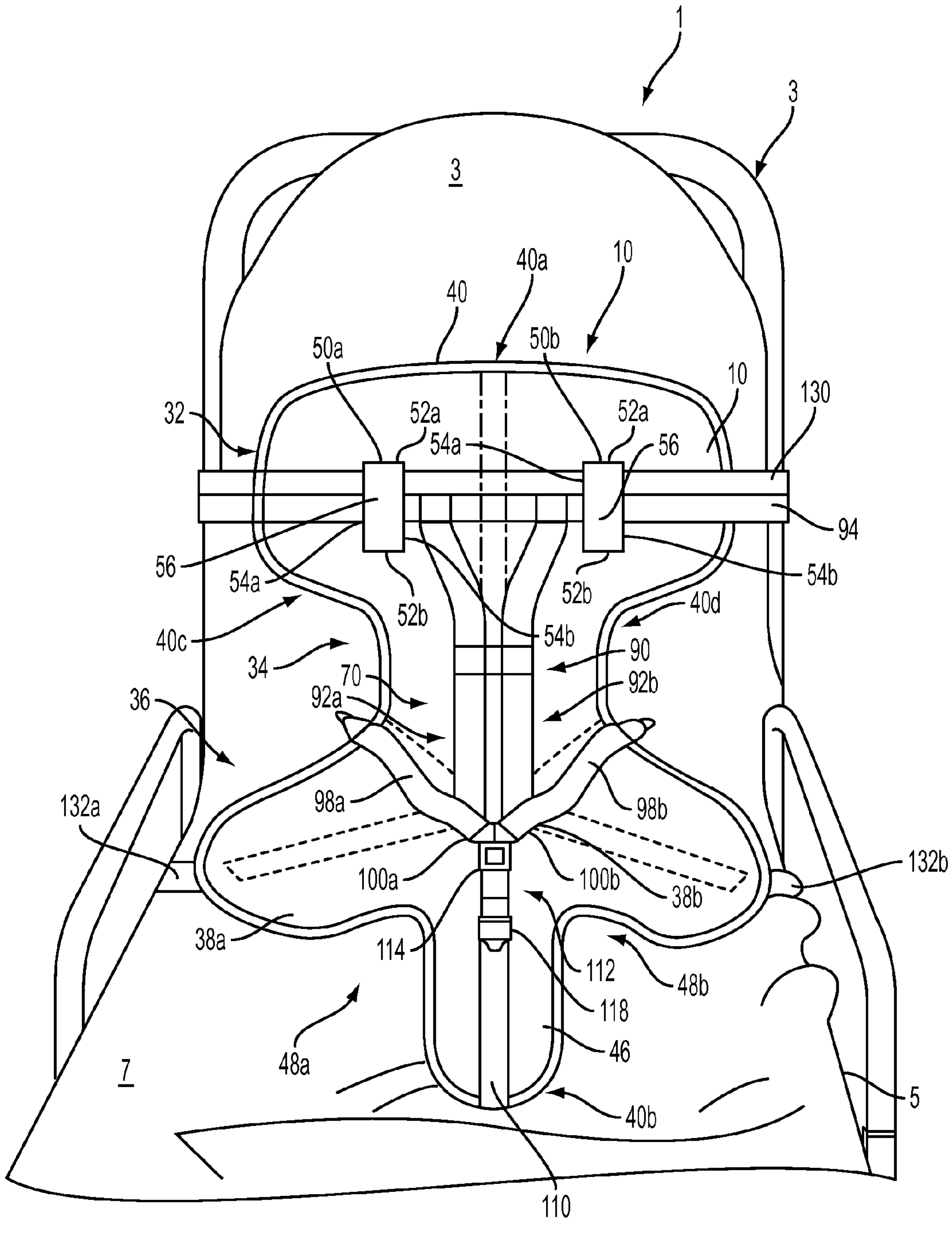
FIG. 8 is a front perspective view of an embodiment of a pediatric transport harness system attached to an emergency cot according to an embodiment of the present disclosure.

In one or more embodiments, a pediatric transport harness system 10 for an emergency cot 1 having a harness support structure 30, at least one stabilizing strap 130, at least two guide straps 50*a*, 50*b*, and a harness restraint 70 is disclosed. With regard to the harness support structure 30, referencing FIGS. 1-3 and 8, the harness support structure 30 is attachable to the emergency cot 1. In some embodiments, the harness support structure 30 includes an upper section 32, a middle section 34, and a lower section 36. The upper section 32 is attachable to, attached to, and/or integral with the middle section 34. The middle section 34 is attachable to, attached to, and/or integral with the lower section 36. In some embodiments, such as is shown in FIGS. 1 and 8, at least a portion of the upper section 32 tapers to the middle section 34 and at least a portion of the lower section 36 tapers to the middle section 34. In one or more embodiments, the harness support structure 30 includes an outer edge 40, a pediatric patient contact surface 42, and an emergency cot contact surface 44. The outer edge 40 includes an upper outer edge surface 40*a*, a lower outer edge surface 40*b*, and opposing side outer edge surfaces 40*c*, 40*d*. Referring to FIG. 1, the harness support structure 30 may define a central vertical axis Y. In some embodiments, the central vertical axis Y is an axis of symmetry Y.

With reference to FIGS. 1 and 8, in one or more embodiments, the lower section 36 includes a plurality of subsections 38*a*, 38*b*, and 46. In some embodiments, the plurality of subsections 38*a*, 38*b*, and 46 include opposing side subsections 38*a*, 38*b* and a downward subsection 46. Each of the side subsections 38*a*, 38*b* are attachable to, attached to, and/or integral with the downward subsection 46. In this way, the downward subsection 46 is in between the side subsections 38*a*, 38*b*. In some embodiments, each of the side subsections 38*a*, 38*b* extend outwardly in opposing directions from the central vertical axis Y and/or the axis of symmetry Y of the harness support structure 30. In some embodiments, at least a portion of each of the side subsections 38*a*, 38*b* and the downward subsection 46 is rounded. In further embodiments, each of the side subsections 38*a*, 38*b* and the downward subsection 46 is a distinct projection. Referencing FIGS. 1 and 8, in some embodiments, the side subsections 38*a*, 38*b* and the downward subsection 46 define gaps 48*a*, 48*b* therebetween. As discussed in greater detail below, the gaps 48*a*, 48*b* may function to accommodate the legs of a pediatric patient 150 secured to the pediatric transport harness system 10.

In some embodiments, the harness support structure 30 is substantially planar. In further embodiments, the harness support structure 30 is substantially flexible and is formed from a flexible and/or lightweight material, e.g., a plastic material and/or vinyl polymers.

With reference to FIGS. 1 and 6-9, in one or more embodiments, at least one stabilizing strap 130 is attached to and/or slidably engaged or movably connected with the harness support structure 30. In further embodiments, the stabilizing strap 130, i.e., the upper section stabilizing strap 130, is attached to and/or slidably engaged or movably connected with the upper section 32 of the harness support structure 30 and is attachable to the emergency cot 1. In some embodiments, the upper section stabilizing strap 130 is attached to and/or slidably engaged or movably connected with the upper section 32 of the harness support structure such that it is approximately normal to the lengths $L_1$, $L_2$ of the guide straps 50*a*, 50*b* (discussed in greater detail below). In further embodiments, the upper section stabilizing strap 130 is attachable to a backrest panel section 3 of the emergency cot 1. In some embodiments, the upper section stabilizing strap 130 is slidably engaged with the guide straps 50*a*, 50*b* (discussed in greater detail below) such that the upper section stabilizing strap 130 may be freely translated from one of the end portions thereof 52*a* to the remaining end portion thereof 52*b* along the lengths $L_1$, $L_2$ of the guide straps. Translation may be accomplished without the use of a tool and/or mechanical action. In further embodiments, translation of the upper section stabilizing strap 130 along the lengths $L_1$, $L_2$ of the guide straps 50*a*, 50*b* is such that the upper section stabilizing strap 130 may be continuously positioned, secured, and/or attached to the emergency cot 1 at all points along the lengths $L_1$, $L_2$ of the guide straps 50*a*, 50*b*.

Figure 9:
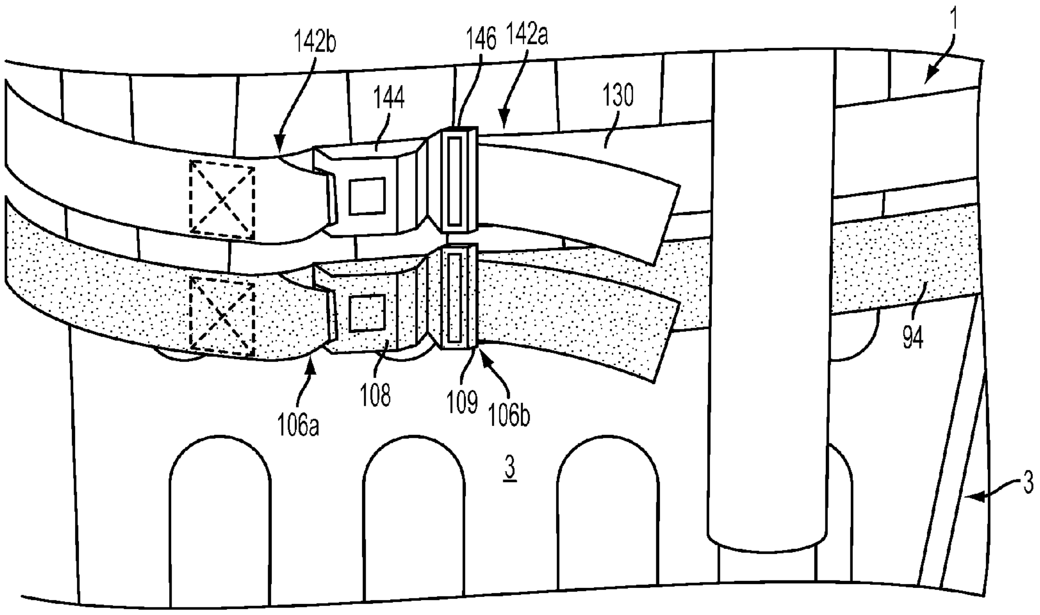
FIG. 9 is back partial perspective view of an embodiment showing attachment of a stabilizing strap and a securing strap to a backrest panel section of an emergency cot according to the present disclosure.

As shown in FIG. 9, the stabilizing strap 130 includes end portions thereof 142*a*, 142*b*. In some embodiments, one end portion 142*b* provides a quick release buckle 144 and the remaining end portion 142*a* provides a tang 146. The tang 146 may be sized to fit through a slot (not shown) of the quick release buckle 144. Referencing FIG. 12, in some embodiments, each of the end portions 142*a*, 142*b* provides a quick release restraint buckle 170*a*, remaining buckle identical, not shown (i.e., the first pair of quick release restraint buckles) mountable to the emergency cot 1 via mounting points 190*a*, remaining mounting point identical, not shown (i.e., the first pair of mounting points). Each of the quick release restraint buckles 170*a*, not shown, (as well as the quick release restraint buckles described in greater detail below) may be as described in U.S. Pub. No. 2010/0175702 (U.S. application Ser. No. 12/377,133), the contents of which are hereby incorporated by reference in their entirety. More particularly, each of the quick release restraint buckles 170*a*, not shown, provides a keyhole shaped slot 172 with an upper slot section 174*a* which tapers down to a lower slot section 174*b*. In some embodiments, the upper slot section 174*a* and the lower slot section 174*b* are separated by the pair of detents 174*c*. In other embodiments, the upper slot section 174*a* tapers to the pair of detents 174*c*. The pair of detents 174*c* may be sized to snap fit a mounting point provided to the emergency cot 1 from the upper slot section 174*a* to the lower slot section 174*b*.

Each of the respective mounting points 190*a*, not shown, may include a stem portion 192 and a cap portion 194. In one or more embodiments, the cap portion 194 is wider than the lower slot section 174*b*, ensuring that the quick release restraint buckle 170*a*, not shown, cannot slip off the mounting point 190*a*, not shown. Additionally, the pair of detents 174*c* may be slightly narrower than the diameter of the stem portion 192 of each of the respective mounting points 190*a*, not shown. In some embodiments, due to the narrower detent section 174*c*, positioning the stem portion 192 in the upper slot section 174*a* and pulling upwards on the quick release restraint buckle 170*a*, not shown, will snap fit the stem portion 192 past the detent section 174*c* and be retained via an interference fit with the detent section 174*c* in the lower slot section 174*b*. The snap fit employed by the quick release restraint buckles 170*a*, not shown, according to the present disclosure, may permit quick releasing of the buckles 170*a*, not shown, without the use of a tool.

In some embodiments, the first pair of mounting points 190*a*, not shown, for the upper section stabilizing strap 130 is provided on lateral sides 12 of the backrest panel section 3 of the emergency cot 1. In other embodiments, the mounting points 190*a*, not shown, for the upper section stabilizing strap 130 are located at any place on the emergency cot 1 that is convenient in securing the first pair of quick release restraint buckles, 170*a*, not shown, to the cot 1 such that they provide suitable use of the upper section stabilizing strap 130 to the respective mounting points, 190*a*, not shown. In other embodiments, the mounting points, 190*a*, not shown, are located at any place on the cot 1 that is convenient in securing the quick release restraint buckles, 170*a*, not shown, to the cot 1 such that they provide suitable use of the upper section stabilizing strap 130.

In one or more embodiments, the stabilizing strap 130 includes a strap length adjuster (not shown) provided thereto. In some embodiments, the at least one stabilizing strap 130 is flexible and is formed from a flexible and/or durable material.

Referencing FIGS. 2, 4-5, 7, and 10 in some embodiments, the pediatric transport harness system 10 includes a plurality of stabilizing straps 130, 132*a*, 132*b*. More particularly, in addition to the upper section stabilizing strap 130, the pediatric transport harness system 10 includes at least two additional stabilizing straps 132*a*, 132*b*, i.e., the lower section stabilizing straps 132*a*, 132*b*, attached to the lower section 36 of the harness support structure 30 and attachable to the emergency cot 1. In further embodiments, the lower section stabilizing straps 132*a*, 132*b* are attachable to respective side rails 9*a*, 9*b* of the emergency cot 1. In some embodiments, each of the lower section stabilizing straps 132*a*, 132*b* is respectively attached to the opposing side subsections 38*a*, 38*b* of the harness support structure 30. In one or more embodiments, the lower section stabilizing straps 132*a*, 132*b* include respective end portions thereof 134*a*, 134*b*. One end portion 134*a* may provide a quick release buckle 136, and the remaining end portion 134*b* may provide a tang 138. Each tang 138 of the lower section stabilizing straps 132*a*, 132*b* is sized to fit through a slot (not shown) of each of the quick release buckles 136 of the lower section stabilizing straps 132*a*, 132*b*.

Figure 14:
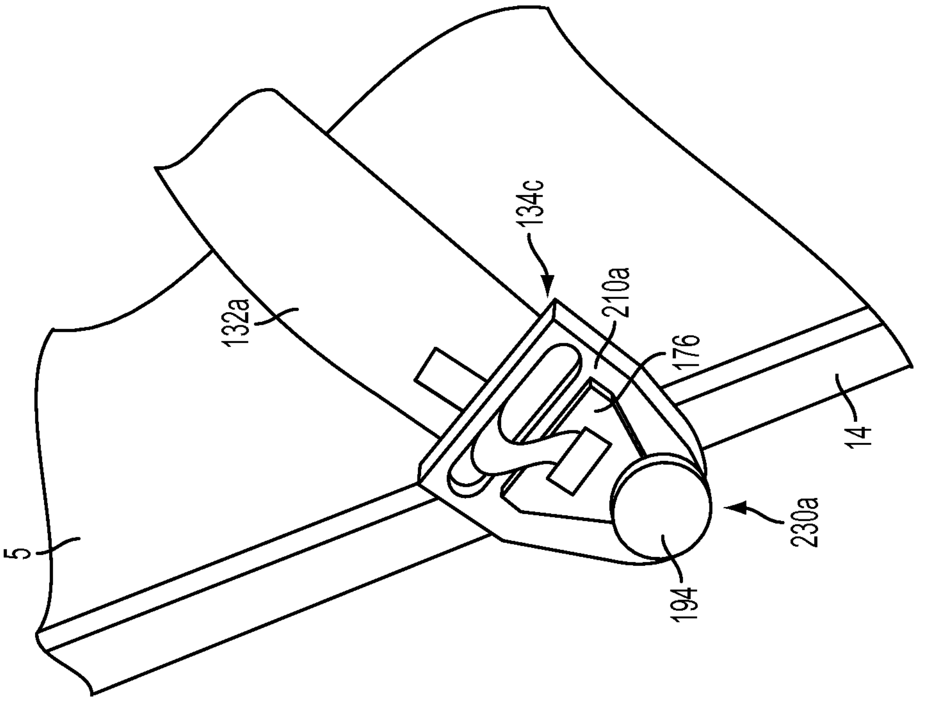
FIG. 14 is a side elevated, partial perspective view of an embodiment of the retaining plug of FIG. 13 properly fitted in place.
Figure 13:
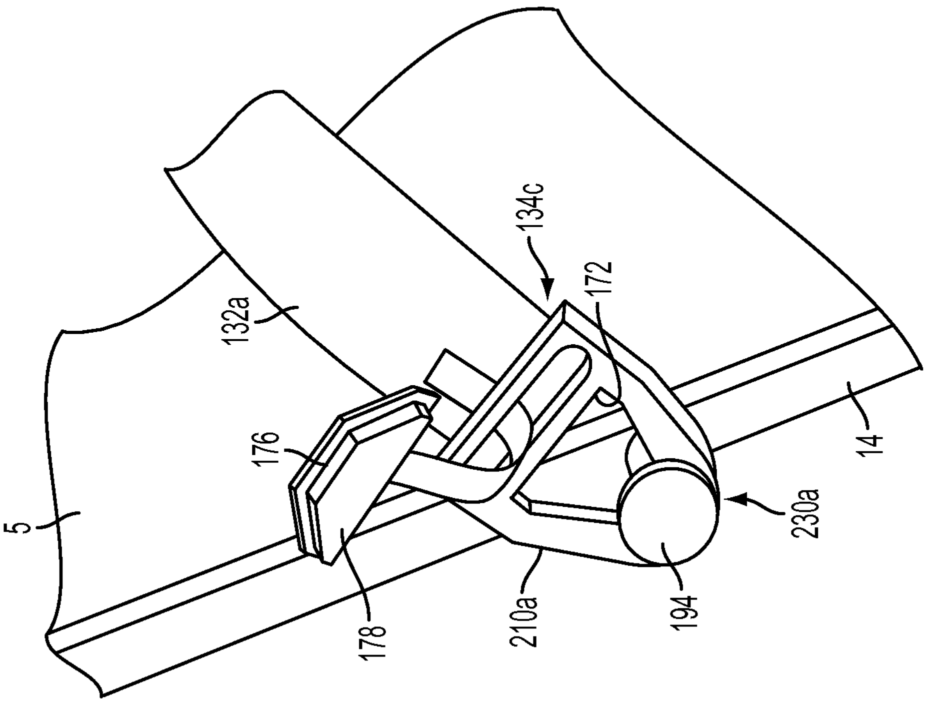
FIG. 13 is a side elevated, partial perspective view of an embodiment showing fitting of a retaining plug of a quick release restraint buckle provided by the lower section stabilizing strap.

Referencing FIGS. 13-14, in some embodiments, the lower section stabilizing straps 132*a*, 132*b* include a single respective end portion thereof 134*c*. In further embodiments, each end portions 134*c* provides a quick release restraint buckle 210*a*, remaining buckle identical, not shown (i.e., the second pair of quick release restraint buckles 210*a*, not shown) mountable to the emergency cot 1 via mounting points 230*a*, not shown (i.e., the second pair of mounting points 230*a*, not shown). The second pair of quick release restraint buckles 210*a*, not shown, and the second pair of mounting points 230*a*, not shown, is as previously described with regard to the first pair of quick release restraint buckles 170*a*, not shown, and the first pair of mounting points 190*a*, not shown. In some embodiments, the mounting points 230*a*, not shown, are provided on lateral sides 14 of the seat panel section 5 of the emergency cot 1. In other embodiments, the mounting points 230*a*, not shown, for the lower section stabilizing strap 132*a*, 132*b* are located at any place on the emergency cot 1 that is convenient in securing the second pair of quick release restraint buckles, 210*a*, not shown, to the cot 1 such that they provide suitable use of the lower section stabilizing straps 132*a*, 132*b* to the respective mounting points, 230*a*, not shown. In other embodiments, the mounting points, 230*a*, not shown, are located at any place on the cot 1 that is convenient in securing the quick release restraint buckles, 210*a*, not shown, to the cot 1 such that they provide suitable use of the lower section stabilizing straps 132*a*, 132*b*.

In some embodiments, each of the lower section stabilizing straps 132*a*, 132*b* includes a strap length adjuster 140 provided thereto. In some embodiments, the lower section stabilizing straps 132*a*, 132*b* are flexible and are formed from a flexible and/or durable material.

Figure 6:
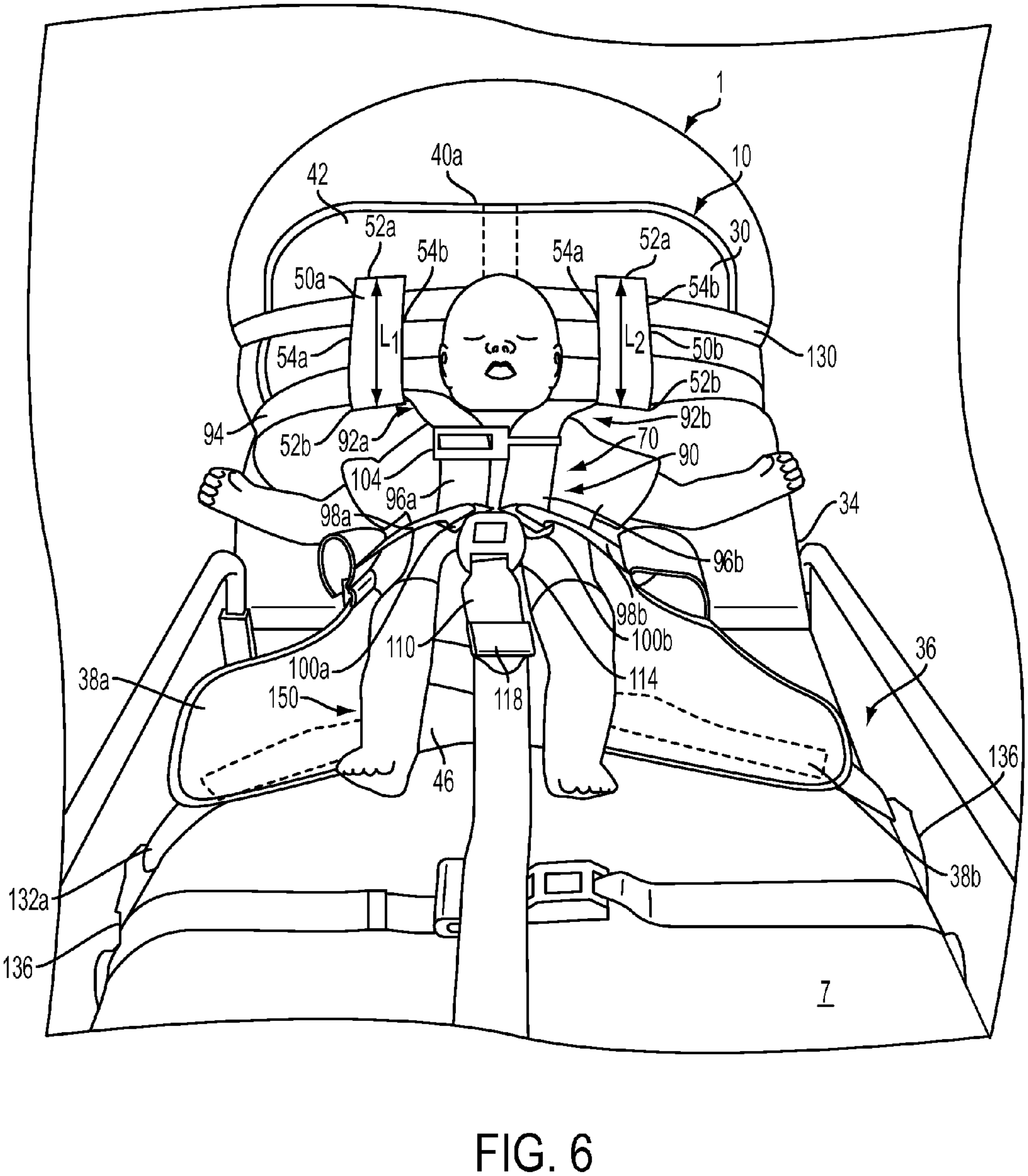
FIG. 6 is a front perspective view of an embodiment of a pediatric transport harness system attached to an emergency cot with a raised backrest panel section and a pediatric patient secured thereon according to an embodiment of the present disclosure.

With reference to FIGS. 1, 6, and 8, in one or more embodiments, at least two guide straps 50*a*, 50*b* are attached to the harness support structure 30. In further embodiments, each of the guide straps 50*a*, 50*b* are attached to the upper section 32 of the harness support structure 30. In still further embodiments, the guide straps 50*a*, 50*b* are attached to the upper section 32 of the harness support structure 30 in substantially corresponding positions. For example, the guide straps 50*a*, 50*b* may be attached to the upper section 32 of the harness support structure 30 such that the guide straps 50*a*, 50*b* are substantially aligned in a vertical direction along the central vertical axis Y and/or such that the guide straps 50*a*, 50*b* are substantially equidistant from the central vertical axis Y of the harness support structure 30.

Still referencing FIGS. 1, 6, and 8, each of the guide straps 50*a*, 50*b* includes end portions thereof 52*a*, 52*b*, side surfaces thereof 54*a*, 54*b*, and a middle section 56 thereof. As shown in FIG. 1, in one or more embodiments, each of the guide straps 50*a*, 50*b* includes a length $L_1$, $L_2$ extending from one of the end portions 52*a* to the remaining end portion 52*b*. In some embodiments, the end portions 52*a*, 52*b* of each of the guide straps 50*a*, 50*b* are attached to and/or integral with the upper section 32 of the harness support structure 30 such that the middle sections 56 are separated from and/or spaced apart from the harness support structure 30. In further embodiments, the middle sections 56 are separated from and/or spaced apart from the pediatric patient contact surface 42 of the harness support structure 30.

In some embodiments, the guide straps 50*a*, 50*b* are flexible and are formed from a flexible and/or durable material.

Referencing FIGS. 1, 3, and 5-6, in one or more embodiments, a harness restraint 70 is attached to the harness support structure 30. In further embodiments, the harness restraint 70 is attached to the middle section 34 and to the lower section 36 of the harness support structure 30. In one or more embodiments, the harness restraint 70 includes a torso harness 90 and a crotch strap 110. The torso harness 90 is attachable to the crotch strap 110.

Figure 11:
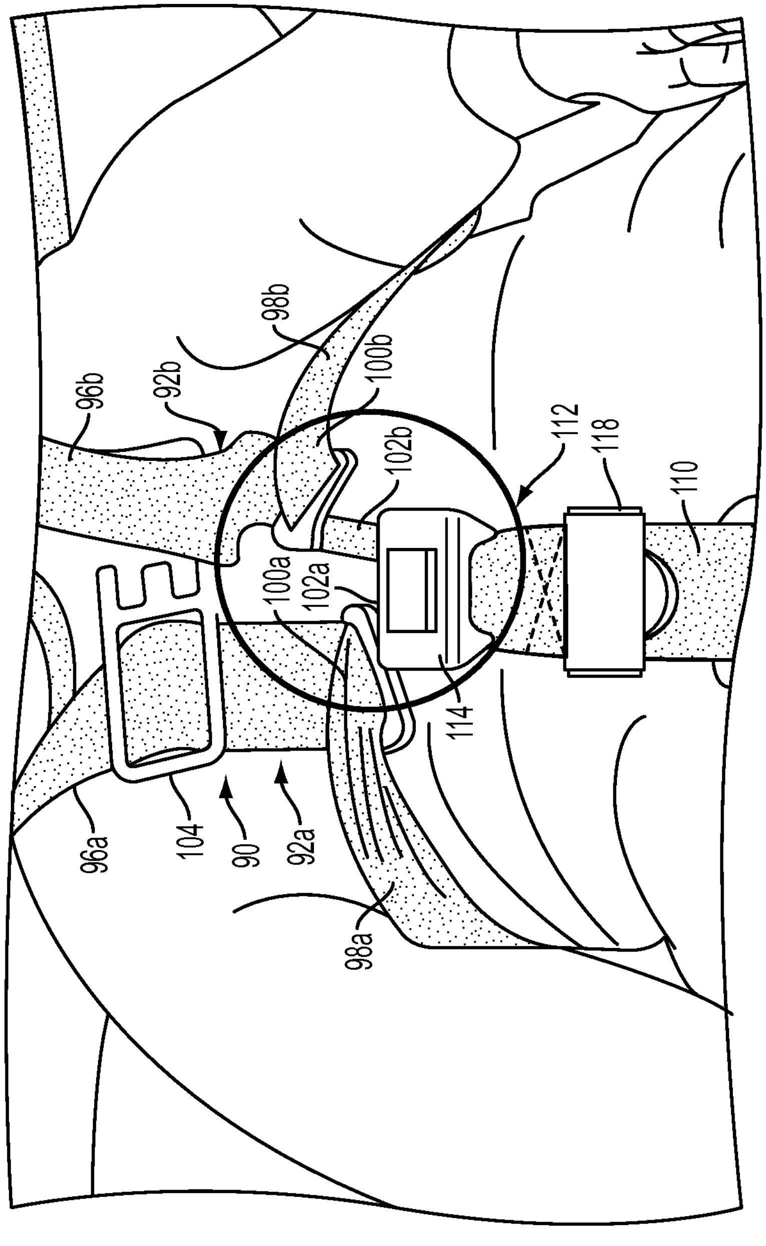
FIG. 11 is a front partial perspective view of an embodiment showing attachment of the torso straps to the crotch strap according to the present disclosure.

Referencing FIGS. 1, 3, and 5-6, in some embodiments, the torso harness 90 is attached to the harness support structure 30. In further embodiments, the torso harness 90 is attached to the middle section 34 of the harness support structure 30. The torso harness 90 includes a pair of torso straps 92*a*, 92*b* and a securing strap 94. The torso straps 92*a*, 92*b* are attachable to, attached to, and/or integral with the securing strap 94. As shown in FIGS. 1, 8, and 11, in one or more embodiments, the torso straps 92*a*, 92*b* are twisted. Each of the torso straps 92*a*, 92*b* includes a shoulder strap segment 96*a*, 96*b*, a pelvis strap segment 98*a*, 98*b*, and a twisted strap segment 100*a*, 100*b*. In one or more embodiments, each of the shoulder strap segments 96*a*, 96*b* is respectively attachable to, attached to, and/or integral with one of the twisted strap segments 100*a*, 100*b*, and each of the twisted strap segments 100*a*, 100*b* is respectively attachable to, attached to, and/or integral with one of the pelvis strap segments 98*a*, 98*b*. In this way, the torso straps 92*a*, 92*b* provide a continuous-loop from the shoulder strap segments 96*a*, 96*b* to the twisted strap segments 100*a*, 100*b* to the pelvis strap segments 98*a*, 98*b*. In some embodiments, each of the shoulder strap segments 96*a*, 96*b* is attached to the securing strap 94, each of the pelvis strap segments 98*a*, 98*b* is attached to the middle section 34 of the harness support structure 30, and each of the twisted strap segments 100*a*, 100*b* is attachable to the crotch strap 110. Referring now to FIGS. 1 and 11, in one or more embodiments, each of the torso straps 92*a*, 92*b* provides a tang 102*a*, 102*b*. In more particular embodiments, each of the twisted strap segments 100*a*, 100*b* provides a tang 102*a*, 102*b*.

As shown in FIGS. 1, 3, 5, and 11 the pediatric transport harness system 10 may include a shoulder strap retaining member 104, e.g., a strap clip. The shoulder strap retaining member 104 is attachable to the torso straps 92*a*, 92*b* and functions to retain the torso straps 92*a*, 92*b* of the torso harness 90 in a substantially fixed position. In some embodiments, the shoulder strap retaining member 104 is attachable to the shoulder strap segments 96*a*, 96*b* of the torso straps 92*a*, 92*b*. Additionally, as shown in FIG. 1, each of the torso straps 92*a*, 92*b* may also include a strap length adjuster 116*a*, 116*b* provided thereto.

In some embodiments, the torso straps 92*a*, 92*b* are flexible and are formed from a flexible and/or durable material.

Figure 5:
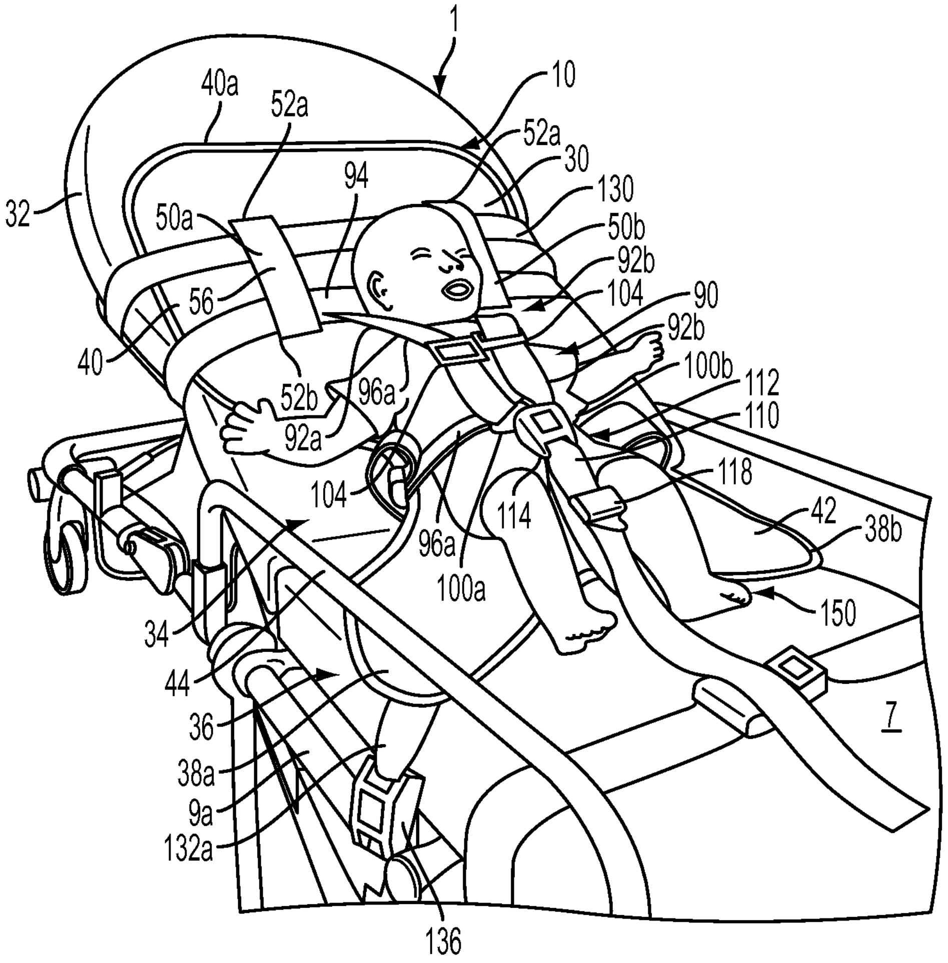
FIG. 5 is a side perspective view of an embodiment of a pediatric transport harness system attached to an emergency cot with a raised backrest panel section and a pediatric patient secured thereon according to an embodiment of the present disclosure.
Figure 7:
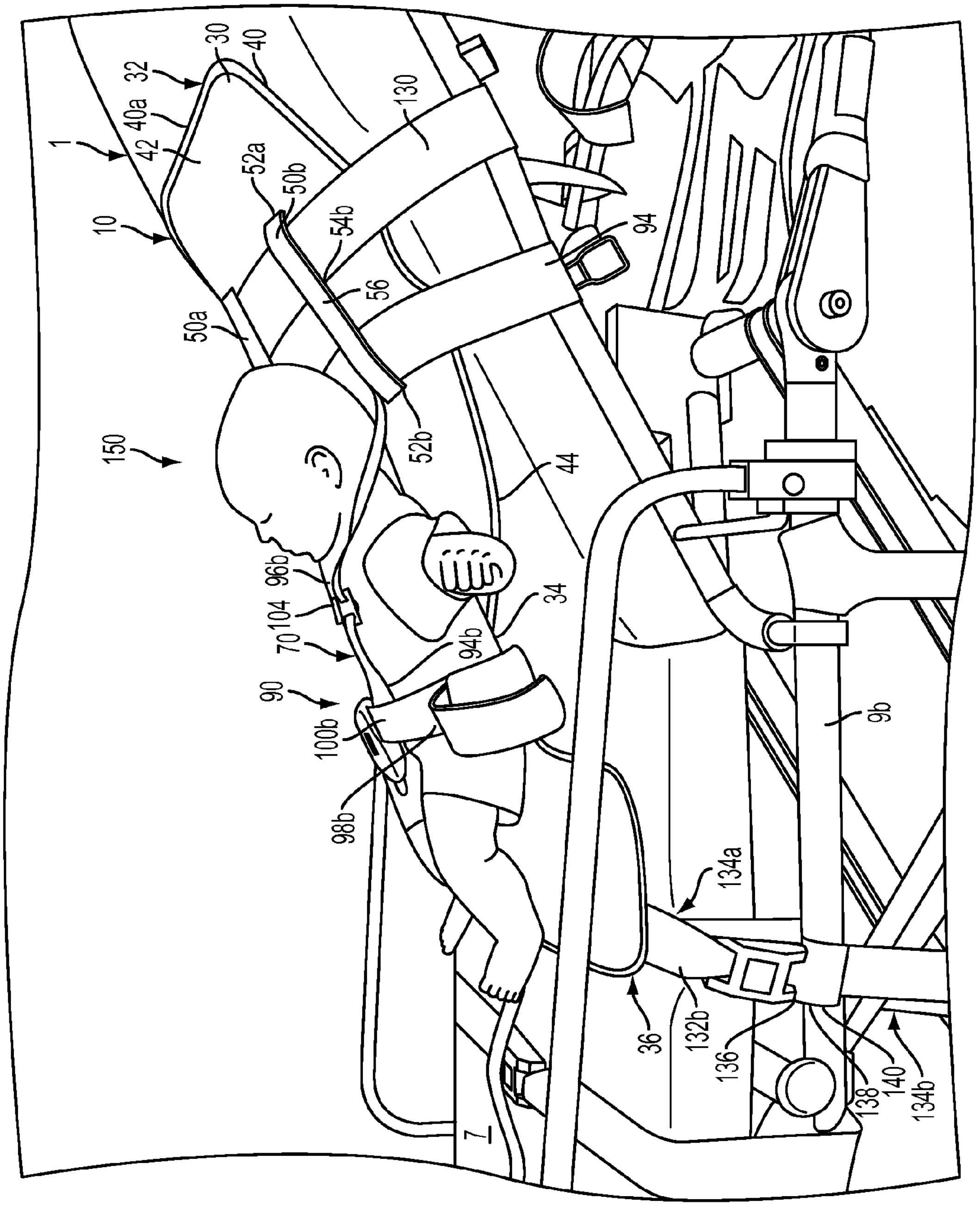
FIG. 7 is a side view of an embodiment of a pediatric transport harness system attached to an emergency cot with a pediatric patient secured thereon according to an embodiment of the present disclosure.

Referring now to FIGS. 1, 5, and 7, the securing strap 94 is slidably engaged and/or movably connected with the guide straps 50*a*, 50*b* and is attachable to the emergency cot 1. In further embodiments, the securing strap 94 is attachable to the backrest panel section 3 of the emergency cot 1. In some embodiments, the securing strap 94 is slidably engaged with the guide straps 50*a*, 50*b* such that the securing strap 94 is positioned in between the guide straps 50*a*, 50*b* and the pediatric patient contact surface 42 of the harness support structure 30. In one or more embodiments, the securing strap 94 is slidably engaged with the guide straps 50*a*, 50*b* such that the securing strap 94 is approximately normal to the lengths $L_1$, $L_2$ of the guide straps 50*a*, 50*b*. As discussed in greater detail below, the securing strap 94 is slidably engaged with the guide straps 50*a*, 50*b* such that the securing strap 94 may be freely translated from one of the end portions 52*a* to the remaining end portion 52*b* of the guide straps 50*a*, 50*b* along the lengths $L_1$, $L_2$ thereof. Translation of the securing strap 94 may be accomplished without the use of a tool and/or mechanical action. In further embodiments, translation of the securing strap 94 along the lengths $L_1$, $L_2$ of the guide straps 50*a*, 50*b* is such that the securing strap 94 may be continuously positioned, secured, and/or attached to the emergency cot 1 at all points along the lengths $L_1$, $L_2$ of the guide straps 50*a*, 50*b*.

As shown in FIG. 9, the securing strap 94 includes end portions thereof 106*a*, 106*b*. In some embodiments, one end portion 106*a* provides a quick release buckle 108 and the remaining end portion 106*b* provides a tang 109. The tang 109 may be sized to fit through a slot (not shown) of the quick release buckle 108.

Figure 12:
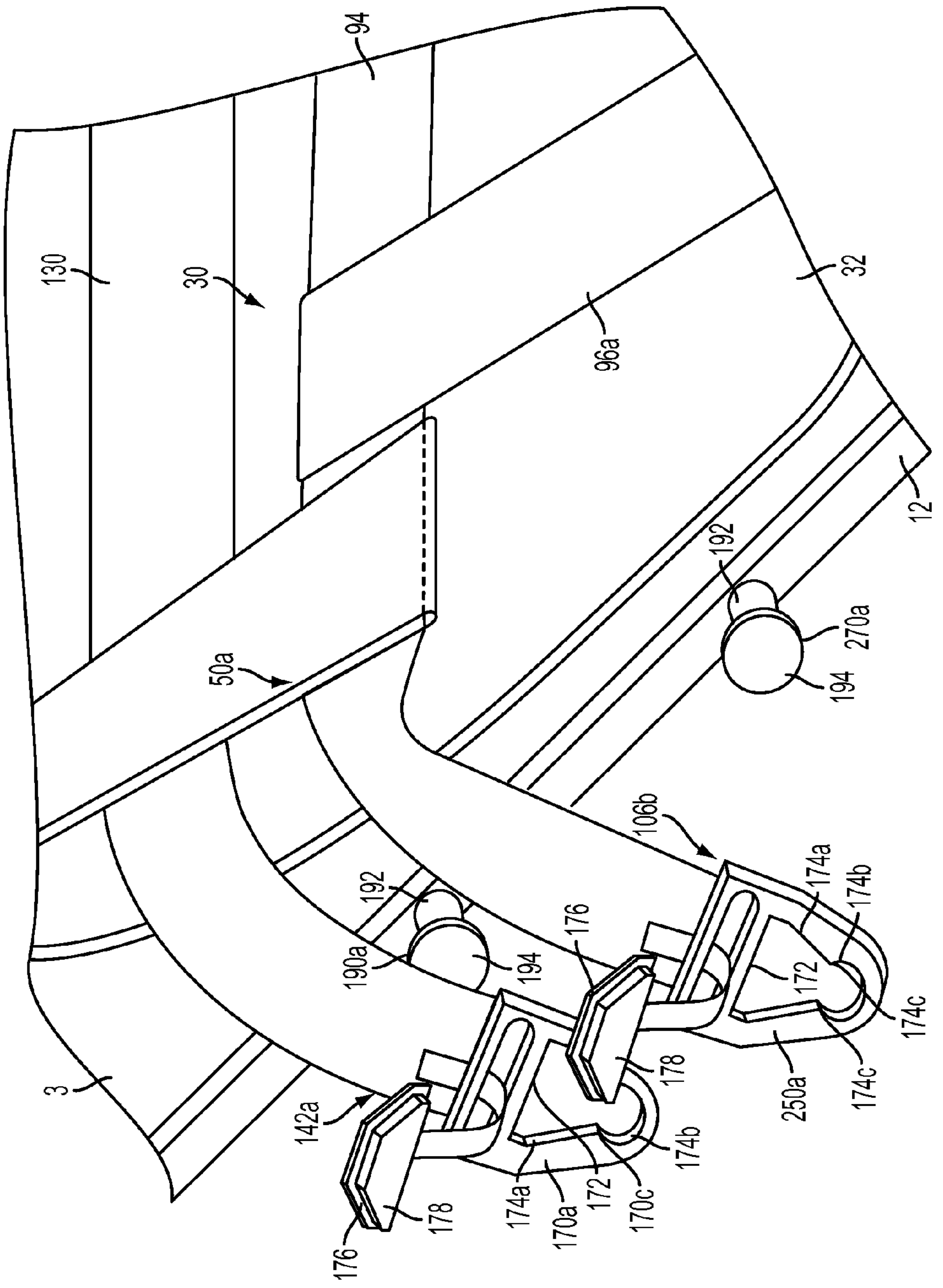
FIG. 12 is a side elevated, partial perspective view of an embodiment showing fitting of a quick release restraint buckles provided by the upper section stabilizing strap and the securing strap.

Referencing FIG. 12, in some embodiments, each of the end portions 106*a*, 106*b* provides a quick release restraint buckle 250*a*, remaining buckle identical, not shown (i.e., the third pair of quick release restraint buckles 250*a*, not shown) mountable to the emergency cot 1 via mounting points 270*a*, not shown, (i.e., the third pair of mounting points 270*a*, not shown). The third pair of quick release restraint buckles 250*a*, not shown, and the third pair of mounting points 270*a*, not shown, is as previously described with regard to the first and second pair of quick release restraint buckles 170*a*, not shown, 210*a*, not shown and the first and second pair of mounting points 190*a*, not shown, 230*a*, not shown. In some embodiments, the third pair of mounting points 270*a*, not shown, is provided on lateral sides 12 of the backrest panel section 3 of the emergency cot 1. In other embodiments, the mounting points 270*a*, not shown, for the securing strap 94 are located at any place on the emergency cot 1 that is convenient in securing the third pair of quick release restraint buckles, 250*a*, not shown, to the cot 1 such that they provide suitable use of the securing strap 94 to the respective mounting points, 270*a*, not shown. In other embodiments, the mounting points, 270*a*, not shown, are located at any place on the cot 1 that is convenient in securing the quick release restraint buckles, 250*a*, not shown, to the cot 1 such that they provide suitable use of the securing strap 94.

In one or more embodiments, the securing strap 94 includes a strap length adjuster (not shown) provided thereto. In some embodiments, the securing strap 94 is flexible and is formed from a flexible and/or durable material.

Referencing FIGS. 12-14, each of the quick release restraint buckles 170*a*, not shown, 210*a*, not shown, 250*a*, not shown (e.g., to each of the first, second, and/or third pair of quick release restraint buckles) may provide a retaining plug 176 to avoid an unintentional release. In some embodiments, the retaining plug 176 has a plug portion 178 sized to fit securely in the upper slot section 174*a* of the plurality of quick release restraint buckles 170*a,* not shown, 210*a,* not shown, 250*a,* not shown. In other embodiments, the retaining plug 176 has a plug portion 178 shaped to fit tightly in the upper slot section 174*a* of the plurality of quick release restraint buckles 170*a,* not shown, 210*a,* not shown, 250*a,* not shown. The plug portion 178 may correspond in size and/or shape to the upper slot section 174*a* of the plurality of quick release restraint buckles 170*a,* not shown, 210*a,* not shown, 250*a,* not shown, such that it fits securely therein. With specific reference to FIG. 14, with the plug portion 178 pushed into the upper slot section 174*a,* the retaining plug 176 prevents an unintentional downward pull on the restraint buckle 210*a* from quick releasing the stem portion 192 of the mounting points 230*a* from the lower slot section 174*b.*

As shown in FIGS. 1, 3, 5-7, and 11, the crotch strap 110 is attached to the harness support structure 30. In further embodiments, the crotch strap 110 is attached to the lower section 36 of the harness support structure 30. In still further embodiments, the crotch strap 110 is attached to downward subsection 46 of the lower section 36. In some embodiments, the crotch strap 110 is attached to the emergency cot contact surface 44 of the downward subsection 46 of the lower section 36. The crotch strap 110 includes an end portion 112. In some embodiments, the end portion 112 provides a quick release buckle 114. The crotch strap 110 is attachable to the torso harness 90 via the torso straps 92*a,* 92*b.* More particularly, the crotch strap 110 is attachable to the torso harness 90 via the tangs 102*a,* 102*b* of the torso straps 92*a,* 92*b.* In these embodiments, the tangs 102*a,* 102*b* are sized to fit through a slot (not shown) of the quick release buckle 114 for releasable attachment of the torso straps 92*a,* 92*b* to the crotch strap 110. The crotch strap 110 may include a strap length adjuster 118 provided thereto.

In some embodiments, the crotch strap 110 is flexible and is formed from a flexible and/or durable material.

Embodiments of the pediatric transport harness system 10 have now been described in detail. Reference will now be made in detail to embodiments of using, attaching, and unattaching the pediatric transport harness system 10 to the emergency cot 1 and of securing a pediatric patient 150 thereto with reference to FIGS. 1-14.

II. Guidelines for Using the Pediatric Transport Harness System

Figure 3:
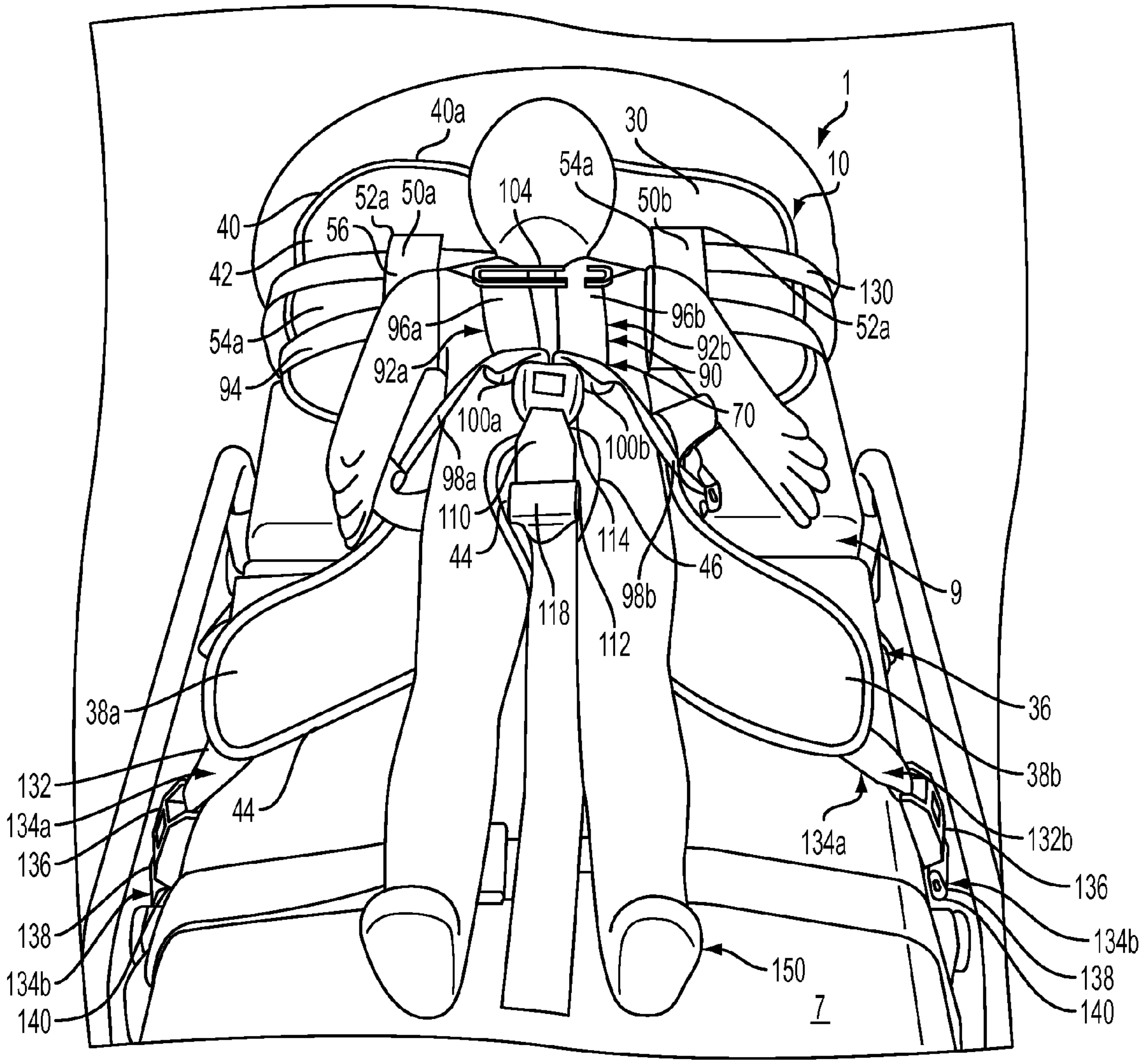
FIG. 3 is a front perspective view of an embodiment of a pediatric transport harness system attached to an emergency cot with a raised backrest panel section and a pediatric patient secured thereon according to an embodiment of the present disclosure.
Figure 4:
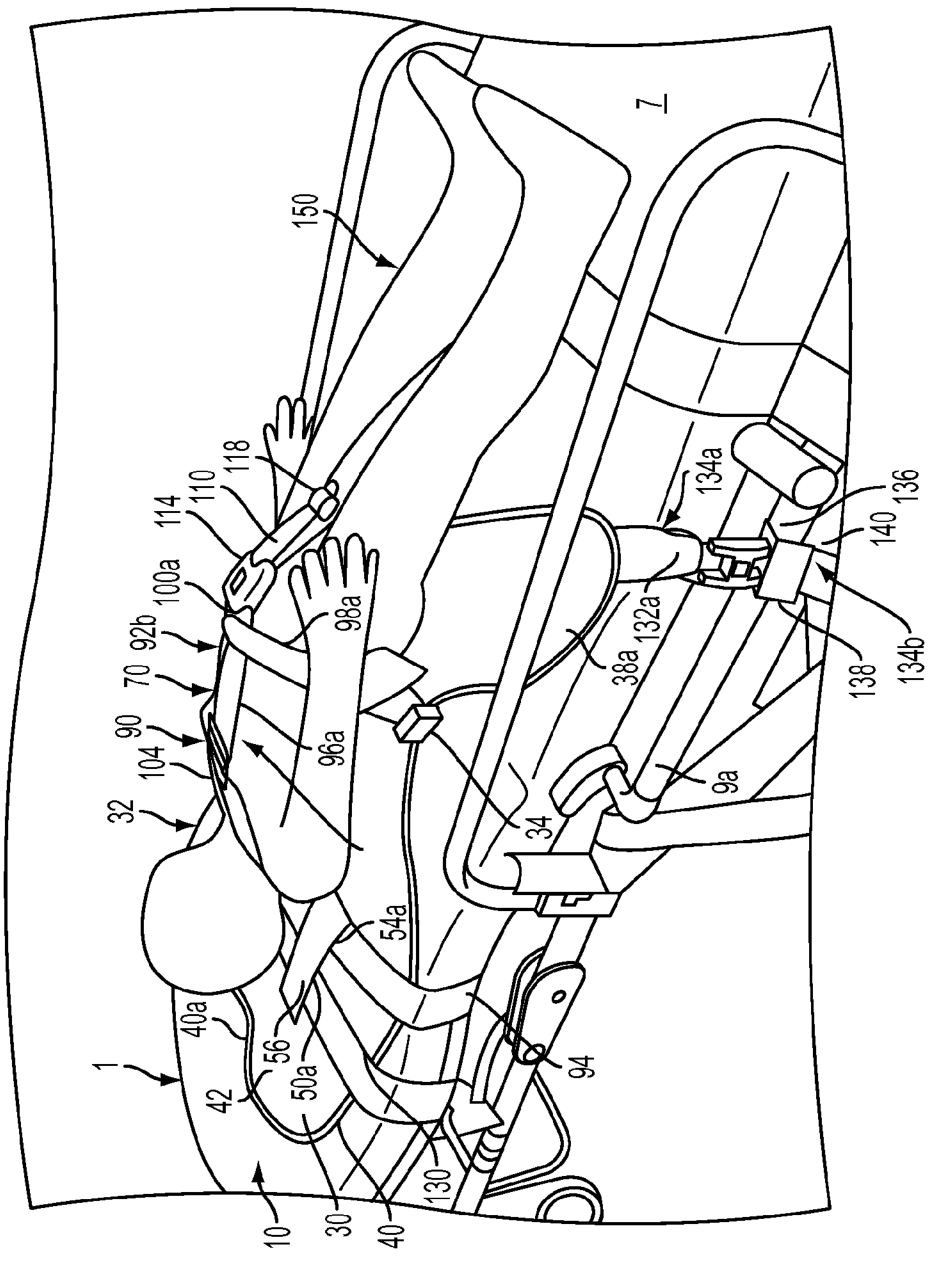
FIG. 4 is a side perspective view of an embodiment of a pediatric transport harness system attached to an emergency cot with a pediatric patient secured thereon according to an embodiment of the present disclosure.

In some embodiments, referring to FIGS. 3 and 6, the pediatric transport harness systems 10 as previously described herein are provided to emergency cots 1 for securing pediatric patients 150 thereto. Pediatric patients 150 properly restrained by such pediatric transport harness systems 10 are shown in FIGS. 3 and 6. The pediatric transport harness systems 10 as previously described herein are suitable for use with pediatric patients 150 such as, e.g., infants and toddlers weighing from approximately 10 to 80 pounds.

To secure a pediatric patient 150 to the pediatric transport harness system 10, the pediatric transport harness system 10 is positioned on and attached to the emergency cot 1. Referencing FIGS. 1 and 8, the pediatric transport harness system 10 is positioned on the emergency cot 1. In order to position the pediatric transport harness system 10 on the emergency cot 1, any restraints attached to the emergency cot 1 should be unattached and removed therefrom. Additionally, depending upon the size of the pediatric patient 150, the backrest panel section 3 of the emergency cot 1 may need to be raised. More particularly, the backrest panel section 3 may be raised such that the shoulders of the pediatric patient 150 are higher than the pelvis of the pediatric patient 150, such that an appropriate center of gravity of the pediatric patient 150 is maintained. In some embodiments, the backrest panel section 3 of the emergency cot 1 is raised at an angle $\alpha$ of between 15 and 45 degrees. The angle $\alpha$ is defined by a plane parallel to the ground and/or emergency cot supporting surface at the height of the seat panel section 5 of the emergency cot 1 and a plane aligned with the backrest panel section 3 of the emergency cot 1.

Where the pediatric transport harness system 10 has been rolled, such as e.g., for compact storage and/or transport, the pediatric transport harness system 10 should be unrolled for positioning on the mattress 7. More particularly, the pediatric transport harness system 10 should be unrolled such that it is substantially flat. Still referencing FIGS. 1 and 8, the unrolled and/or substantially flat pediatric transport harness system 10 may be positioned on the mattress 7 of the emergency cot 1. More particularly, the pediatric transport harness system 10 may be positioned on the mattress 7 of the emergency cot 1 with the stabilizing straps 130, 132, and/or 132*b,* the torso harness 90, and/or the crotch strap 110 unattached and/or extended. In some embodiments, the pediatric transport harness system 10 is positioned on the mattress 7 such that the upper section 32 overlies the backrest panel section 3 of the emergency cot 1, the lower section 36 overlies the seat panel section 5 of the emergency cot 1, and the middle section 34 overlies a bridging section 9 of the emergency cot 1 connecting the backrest panel section 3 to the seat panel section 5. In some embodiments, the harness support structure 30 may be positioned on the mattress 7 of the emergency cot 1 such that it is substantially centered thereon.

Once the harness support structure 30 is suitably positioned on the emergency cot 1, the harness support structure 30 may be attached to the emergency cot 1. More particularly, the harness support structure 30 may be attached to the emergency cot 1 via the stabilizing straps 130, 132*a,* and/or 132*b* and, as discussed in greater detail below, via the securing strap 94. In embodiments wherein the upper section stabilizing strap 130 is slidably engaged or movably connected with the guide straps 50*a,* 50*b,* the upper section stabilizing strap 130 may be slidably translated along the lengths $L_1$, $L_2$ of the guide straps 50*a,* 50*b.* Translation of the upper section stabilizing strap 130 may be accomplished continuously along the lengths $L_1$, $L_2$ of the guide straps 50*a,* 50*b* without repositioning the harness support structure 30 on the emergency cot 1.

Referencing FIG. 9, the upper section stabilizing strap 130 may be lengthened via use of the respective strap length adjuster 140. The end portions 142*a,* 142*b* of the upper section stabilizing strap 130 may be pulled around the mattress 7 to the back of the backrest panel section 3 of the emergency cot 1, such as is shown in FIG. 9. Once within a suitable attachment distance of one another, the tang 146 may be inserted within the slot (not shown) of the quick release buckle 144. The upper section stabilizing strap 130 may be tightened as needed. In embodiments wherein the upper section stabilizing strap 130 provides the first pair of quick release restraint buckles 170*a,* not shown, such as is shown in FIG. 12, the first pair of quick release restraint buckles 170*a,* not shown, may be mounted to the first pair of mounting points 190*a,* not shown, by pulling the first pair of quick release restraint buckles 170*a,* not shown upward to snap fit such buckles in place. The snap fit employed may permit quick releasing of the first pair of quick release restraint buckles 170*a,* not shown, without the use of a tool. Additionally, in embodiments wherein the first pair of quick release restraint buckles 170*a,* not shown, includes retaining plugs 176, the plug portion 178 of the retaining plug 176 may be fitted securely in the upper slot section 174*a* of each of the first pair of quick release restraint buckles 170*a,* not shown.

Figure 10:
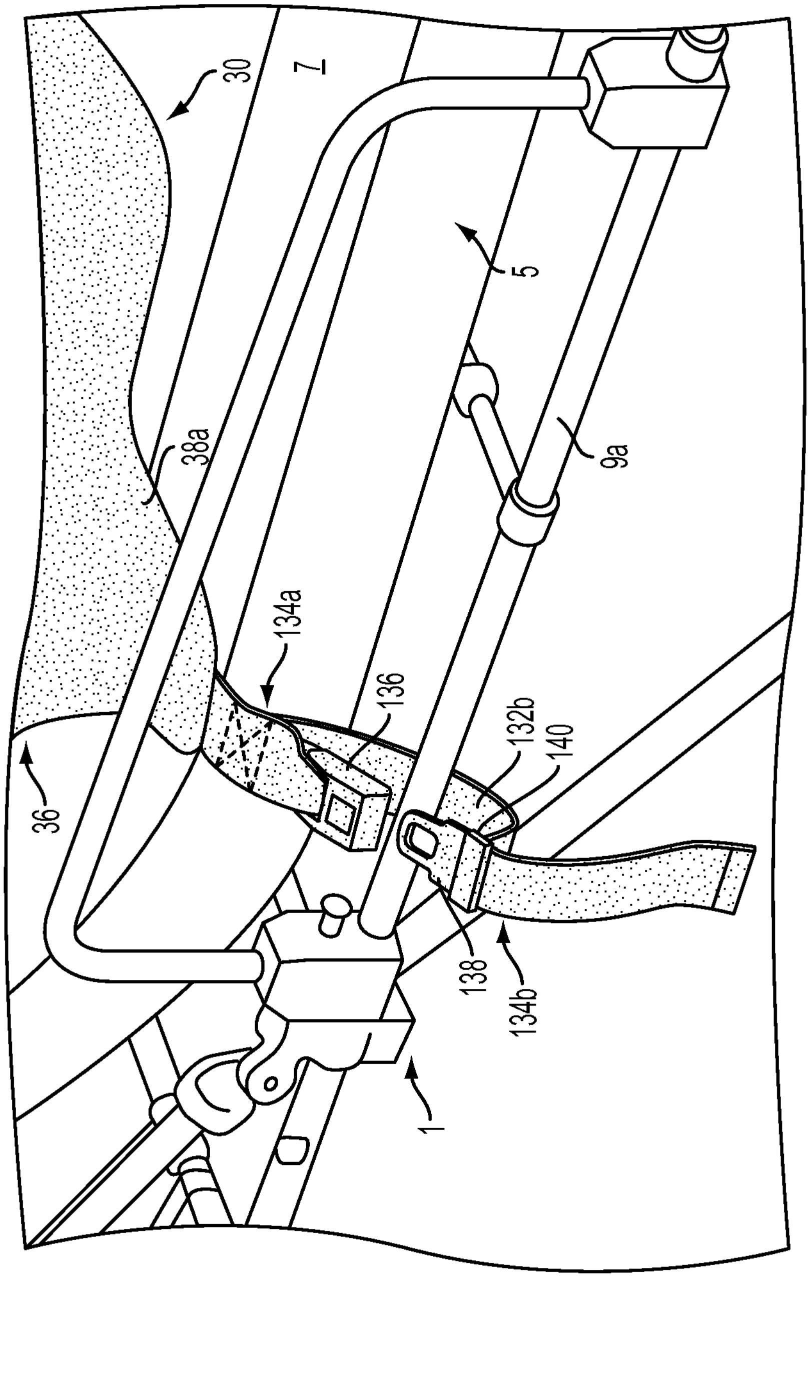
FIG. 10 is a side partial perspective view of an embodiment showing attachment of a stabilizing strap to a side rail of an emergency cot according to the present disclosure.

The lower section stabilizing straps 132*a,* 132*b* may be attached to the emergency cot 1. Referencing FIG. 10, the lower section stabilizing straps 132*a,* 132*b* may be lengthened and/or shortened via the strap length adjusters 140. Upon adjustment of the length of the lower section stabilizing straps 132*a,* 132*b,* the end portions 134*a,* 134*b* of the lower section stabilizing straps 132*a,* 132 may be pulled around respective side rails 9*a,* 9*b* of the emergency cot 1, such as is shown in FIG. 10. Once within a suitable attachment distance of one another, the tang 138 of each of the lower section stabilizing straps 132*a,* 132*b* may be inserted within the slot (not shown) of the respective quick release buckles 136. The lower section stabilizing straps 132*a,* 132*b* may be tightened as needed. In embodiments wherein the lower section stabilizing straps 132*a,* 132*b* provide the second pair of quick release restraint buckles 210*a,* not shown, such as is shown in FIGS. 13-14, the second pair of quick release restraint buckles 210*a,* not shown, may be mounted to the second pair of mounting points 230*a,* not shown, by pulling the second pair of quick release restraint buckles 210*a,* not shown, upward to snap fit such buckles in place. The snap fit employed may permit quick releasing of the second pair of quick release restraint buckles 210*a,* not shown, without the use of a tool. Additionally, in embodiments wherein the second pair of quick release restraint buckles 210*a,* not shown, includes retaining plugs 176, the plug portion 178 of the retaining plug 176 may be fitted securely in the upper slot section 174*a* of each of the second pair of quick release restraint buckles 210*a,* not shown.

Upon attachment of the harness support structure 30 to the emergency cot 1, the pediatric patient 150 may be positioned on the harness support structure 30. The securing strap 94 may be slidably translated along the lengths $L_1$, $L_2$ of the guide straps 50*a,* 50*b* such that it is approximately positioned in alignment with the shoulders of the pediatric patient 150. Translation of the securing strap 94 may be accomplished continuously along the lengths $L_1$, $L_2$ of the guide straps 50*a,* 50*b* without repositioning the harness support structure 30 on the emergency cot 1. In this way, movement of the pediatric patient 150 is minimized and pediatric patients 150 of varying sizes (such as, e.g., varying heights) and weights are accommodated. Upon positioning of the securing strap 94 along the lengths $L_1$, $L_2$, the securing strap 94 may be attached to the emergency cot 1. Referencing FIG. 9, the securing strap 94 may be lengthened and/or shortened via the strap length adjuster (not shown). The end portions 106*a,* 106*b* thereof may be pulled around the mattress 7 to the back of the backrest panel section 3 of the emergency cot 1, such as is shown in FIG. 9. Once within a suitable attachment distance of one another, the tang 109 may be inserted within the slot (not shown) of the quick release buckle 108. The securing strap 94 may be tightened as needed.

In embodiments wherein the securing strap 94 provides the third pair of quick release restraint buckles 250*a,* not shown, such as is shown in FIG. 12, the third pair of quick release restraint buckles 250*a,* not shown, may be mounted to the third pair of mounting points 270*a,* not shown, by pulling the third pair of quick release restraint buckles 250*a,* not shown, upward to snap fit such buckles in place. The snap fit employed may permit quick releasing of the third pair of quick release restraint buckles 250*a,* not shown, without the use of a tool. Additionally, in embodiments wherein the third pair of quick release restraint buckles 250*a,* not shown, includes retaining plugs 176, the plug portion 178 of the retaining plug 176 may be fitted securely in the upper slot section 174*a* of each of the third pair of quick release restraint buckles 250*a,* not shown.

The torso restraint 70 may be placed over the head and/or torso of the pediatric patient 150. Referencing FIGS. 1 and 11, the torso straps 92*a,* 92*b* may be lengthened and/or shortened via the respective strap length adjustors 116*a,* 116*b*. The crotch strap 110 may also be lengthened and/or shortened via the strap length adjustor 118. The end portion 112 of the crotch strap 110 may be pulled between the legs of the pediatric patient 150, such that the legs of the pediatric patient 150 are accommodated by the gaps 48*a,* 48*b* of the harness support structure 30. Respective arms of the pediatric patient 150 may be placed through the respective torso straps 92*a,* 92*b*. Respective tangs 102*a,* 102*b* of the torso straps 92*a,* 92*b* may then be inserted within the slot (not shown) of the quick release buckle 114. The torso straps 92*a,* 92*b* and the crotch strap 110 may be tightened as needed.

Where the pediatric transport harness system 10 includes a shoulder strap retaining member 104, the torso straps 92*a,* 92*b,* and more particularly, the shoulder strap segments 96*a,* 96*b* of the torso straps 92*a,* 92*b,* may be threaded through the shoulder strap retaining member 104. Upon threading therethrough, the shoulder strap retaining member 104 may be slidably translated upwardly toward the head of the pediatric patient 150 to approximately the level of the armpit of the pediatric patient 150. At this point, the pediatric patient 150 is secured to the emergency cot 1 via the pediatric transport harness system 10.

In order to release the pediatric patient 150 from the pediatric transport harness system 10, the crotch strap 110 may be loosened via the strap length adjustor 118. The shoulder strap retaining member 104 may be slidably translated downwardly away from the head of the pediatric patient 150. The torso straps 92*a,* 92*b* and, more particularly, the shoulder strap segments 96*a,* 96*b* of the torso straps 92*a,* 92*b,* may be unthreaded from the shoulder strap retaining member 104. The respective tangs 102*a,* 102*b* may be released from the quick release buckle 114 by pressing the release button 116. The torso straps 92*a,* 92*b* may be loosened with the strap length adjustor 118 as previously discussed. The torso restraint 70 may then be removed from the head and torso of the pediatric patient 150. Upon removal of the torso restraint 70 from the pediatric patient 150, the pediatric patient 150 may be removed from the harness support structure 30.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

It is noted that terms like "preferably," "generally," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

All documents cited are incorporated herein by reference; the citation of any document is not to be construed as an admission that it is prior art with respect to the present disclosure.

It is to be further understood that where descriptions of various embodiments use the term "comprising," and/or "including" those skilled in the art would understand that in some specific instances, an embodiment can be alternatively described using language "consisting essentially of" or "consisting of."

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

What is claimed is:

1. A pediatric transport harness system for an emergency cot comprising:
- a harness support structure attachable to the emergency cot;
- at least one stabilizing strap attached to the harness support structure;
- at least two guide straps attached to the harness support and spanning between a securing strap and the at least one stabilizing strap, wherein:
  - each of the at least two guide straps comprises a first end portion, a second end portion, and a middle portion between the first end portion and the second end portion,
  - each of the at least two guide straps having a length extending from the first end portion to the second end portion,
  - each of the first end portion and the second end portion is attached to the harness support structure, and
  - the middle portion is spaced apart from the harness support structure; and
- a harness restraint attached to the harness support structure, the harness restraint comprising a torso harness and a crotch strap attachable thereto, wherein:
  - the torso harness comprises a pair of torso straps attached to the securing strap, the securing strap being captured between the harness support structure and the middle portion of each of the guide straps such that the securing strap is slidably engaged by the at least two guide straps and may be continuously positioned and secured along the length of the at least two guide straps,
- wherein the at least two guide straps are attached to the harness support structure approximately normal to at least one of the stabilizing strap and the securing strap.

2. The pediatric transport harness system of claim 1, further comprising a plurality of stabilizing straps attached to the harness support structure, wherein the harness support structure is releasably attachable to the emergency cot via the plurality of stabilizing straps and the securing strap.

3. The pediatric transport harness system of claim 1, further comprising a plurality of stabilizing straps attached to the harness support structure, wherein:
- each of the plurality of stabilizing straps comprises a buckle,
- the securing strap comprises a buckle, and
- the harness support structure is releasably attachable to the emergency cot via the buckle of each of the plurality of stabilizing straps and the buckle of the securing strap.

4. The pediatric transport harness system of claim 1, wherein each of the at least two guide straps are attached in corresponding positions to an upper section of the harness support structure.

5. The pediatric transport harness system of claim 1, wherein:
- the torso harness is attached to the harness support structure; and
- the crotch strap is attached to the harness support structure.

6. The pediatric transport harness system of claim 1, wherein each of the pair of torso straps comprises a shoulder strap segment and a pelvis strap segment.

7. The pediatric transport harness system of claim 1, wherein
- each of the pair of torso straps comprises a shoulder strap segment, a twisted strap segment, and a pelvis strap segment;
- the shoulder strap segment of each of the pair of torso straps is attached to the securing strap;
- the pelvis strap segment of each of the pair of torso straps is attached to the harness support structure; and
- the twisted strap segment is attachable to the crotch strap.

8. The pediatric transport harness system of claim 1, wherein the twisted strap segment is attached to a middle section of the harness support structure.

9. The pediatric transport harness system of claim 1, wherein:
- the crotch strap provides a buckle with a slot; and
- each of the pair of torso straps provides a tang sized to be seated releasably in the slot of the buckle.

10. The pediatric transport harness system of claim 1, wherein:
- the harness support structure comprises an upper section, a middle section, and a lower section,
- the upper section tapers to the middle section, and
- the lower section tapers to the middle section, such that when attached to the emergency cot, the upper section overlies a backrest panel section of the emergency cot and the lower section overlies on a seat panel section of the emergency cot.

11. A pediatric transport harness system for an emergency cot comprising:

a harness support structure attachable to the emergency cot, the harness support structure having an upper section, a middle section, and a lower section;

at least one stabilizing strap attached to the harness support structure;

at least two guide straps attached to the upper section of the harness support structure and spanning between a securing strap and the at least one stabilizing strap;

at least two guide straps attached to the upper section of the harness support structure and spanning between a securing strap and the at least one stabilizing strap, wherein:

each of the at least two guide straps comprises a first end portion, a second end portion, and a middle portion between the first end portion and the second end portion, each of the at least two guide straps having a length extending from the first end portion to the second end portion, each of the first end portion and the second end portion is attached to the harness support structure, and the middle portion is spaced apart from the harness support structure; and a harness restraint attached to the middle section of the harness support structure, the harness restraint comprising a torso harness and a crotch strap attachable thereto, wherein:

the torso harness comprises a pair of torso straps attached to the securing strap, each of the pair of torso straps is attached to the middle section of the harness support structure, the crotch strap is attached to the lower section of the harness support structure, the harness support structure is attachable to the emergency cot via the at least one stabilizing strap and the securing strap, and the securing strap is slidably engaged with the at least two guide straps such that the securing strap may be continuously positioned and secured along a length of the at least two guide straps the securing strap is captured between the harness support structure and the middle portion of each of the guide straps such that the securing strap is slidably engaged by the at least two guide straps and may be continuously positioned and secured along the length of the at least two guide straps, wherein the at least two guide straps are attached to the harness support structure approximately normal to at least one of the stabilizing strap and the securing strap.

12. The pediatric transport harness system of claim 11, wherein:

the harness support structure comprises an upper section, a middle section, and a lower section, the upper section tapers to the middle section, and the lower section tapers to the middle section, such that when attached to the emergency cot, the upper section overlies a backrest panel section of the emergency cot and the lower section overlies a seat panel section of the emergency cot.

13. A method of securing a pediatric patient to an emergency cot using the pediatric transport harness system of claim 1, the method comprising:

attaching the harness support structure to the emergency cot via the at least one stabilizing strap and the securing strap;

placing the pediatric patient on the harness support structure;

placing the torso harness over the patient; and attaching the torso harness to the crotch strap thereby securing the pediatric patient to the emergency cot.

14. The method of claim 13, further comprising translating the securing strap along the length of the at least two guide straps from a first position to a second position to accommodate the pediatric patient, and secureably attaching the securing strap in the second position to the emergency cot.

15. The method of claim 13, further comprising adjusting the torso harness and the crotch strap.

16. The method of claim 13, wherein each of the at least one stabilizing strap and the securing strap comprises a buckle such that the harness support structure is attached to the emergency cot via the buckle of each of the at least one stabilizing strap and the securing strap.

17. The method of claim 13, wherein each of the pair of torso straps provides a pair of tangs, wherein the crotch strap provides a buckle with a slot, and wherein the pair of tangs are sized to fit into the slot of the buckle, such that the torso harness is attached to the crotch strap via securing the pair of tangs within the slot of the buckle.

* * * * *